April 5, 1966 M. VAN RENSSELAER Plant Pat. 2,617
MAGNOLIA GRANDIFLORA TREE
Filed Dec. 14, 1964
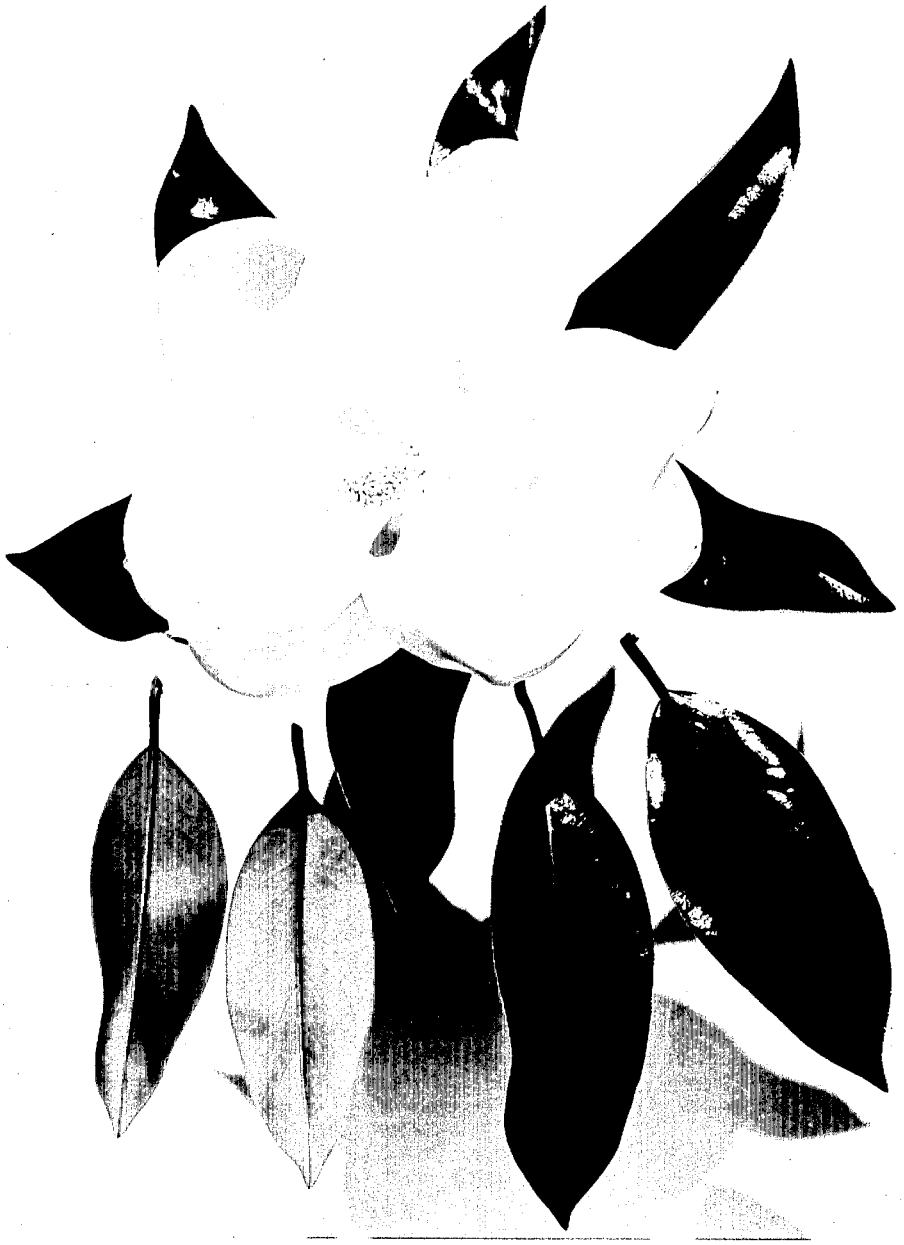
INVENTOR
Maunsell Van Rensselaer
Webster & Webster
ATTYS.

United States Patent Office

Plant Pat. 2,617

Patented Apr. 5, 1966

2,617

MAGNOLIA GRANDIFLORA TREE

Maunsell Van Rensselaer, Saratoga, Calif., assignor to Saratoga Horticultural Foundation, Saratoga, Calif., a non-profit corporation of California Filed Dec. 14, 1964, Ser. No. 418,356
1 Claim. (Cl. Plt.—51)

This invention relates to a new and distinct variety of *Magnolia grandiflora* tree discovered by me at the growing grounds of the Saratoga Horticultural Foundation at Saratoga, California. The new variety was originated as a selected one of a substantial number of seedlings of *Magnolia grandiflora* grown by seeds harvested from trees cultivated in California, the exact parentage being unknown; said new variety having been asexually reproduced in said growing grounds by cuttings and grafting, but chiefly by grafting scions of the new variety on seeding-grown rootstock of *Magnolia grandiflora*.

Asexual reproduction of the new variety has been carried on continuously under my direction since its discovery and in all cases the novel and distinctive characteristics of the new variety have been found to hold true to the original tree.

Several features of this new variety make is distinctive from the many thousands of seedlings and specimens of *Magnolia grandiflora* examined through the years by me in the Western and Southern States of the United States.

*Magnolia grandiflora* is indigenous to the Southern part of the United States from eastern North Carolina, south to Florida, and along the Gulf of Mexico to eastern Texas. It has been widely cultivated in temperate regions of the world. United States plant patents have been issued on two varieties of this species, namely: Samuel Sommer, United States Plant Patent No. 2,015, and Majestic Beauty, United States Plant Patent No. 2,250. The variety herein described is distinct—in particular comparison—from the two above noted patented varieties in several noteworthy characteristics, as follows:

This new variety is especially characterized by the quality of the tomentum on the leaves and elsewhere, and which is far superior in tone, color, and density.

A still further characteristic of the present variety in the bearing of flowers of delicate creamy white color; the flowers normally having twelve petals and being of somewhat smaller size.

The variety is additionally characterized by leaves which are less variable in size and shape.

An additional feature of novelty is the distinct lemon-like fragrance of the flowers.

Other features of comparative difference will be understood from the description hereinafter set forth.

The drawing comprises an illustration, by photographic reproduction in color, of one of the flowers, together with leaves.

Referring now more specifically to the botanical details of this new and distinct variety of *Magnolia grandiflora* tree, the following is an outline description thereof; all major color plate identifications being by reference to Nickerson Color Fan, except where common terms of color definition are employed.

Family: Magnoliaceae.
Parentage: Unknown.
Type: Seedling.
Trunk: The sturdy trunk is smooth, light grey in color, and has thin appressed scales.

*Size and rate of growth*: The ultimate size has not yet been determined, but it can be expected to attain a height of 40 to 50 feet under relatively good conditions. It is strong growing and, where tested, does well under a varied range of soil conditions. Rate of growth is from 18 to 30 inches annually, depending on environment. In central California where this new variety has been tested and evaluated, it has a growth period of approximately six months—from early May to late October. Hardiness has not been fully tested, but most forms of the species are hardy to 15° F. or less.

Foliage: Evergreen.

*Texture.*—Thick and leathery. Much less susceptible to burning during periods of abnormal heat or to bruising by strong winds than most forms of the species.

*Shape.*—Elliptic, acute, and tapering at the base. Plane with no undulation. Margin entire with narrow, yellow-green hyaline band.

*Size.*—Blade varies from 4¾" to 6¾" in length, 2" to 2¾" in width. The petiole varies from ⅞" to 1¼" in length.

The leaves on specimen trees of the new variety are not as variable in size and shape as on most trees of the species.

*Color.*—Upper surface is a glossy, moderate olive green (7.5GY 5/7). Primary vein conspicuous, but not the lateral veins. The narrow, translucent yellow band clearly outlining the margin of each leaf adds to their decorative value when used in bouquets, centerpieces, or other arrangements.

The dominant color is in the tomentum on the under surface of the leaves which is described separately below.

Tomentum: A dense coating of velvety, brownish orange, suede-like tomentum (5YR 5/8) covers the underside of the leaves, the petioles, the branchlets, and the buds of the current season—a novel feature which adds a singular tricolor note of beauty to the ornamental and decorative qualities of this new variety. The tomentum on the protruding primary vein is slightly accentuated with a deeper orange color. The quality of tomentum, in tone of color and in density, is one of the salient characteristics which affords ornamental and decorative beauty to the present variety. Among the countless specimens of *Magnolia grandiflora* examined in the Southern United States, where it is indigenous, and in the Western United States, where it is widely cultivated, none has been found by me to compare in the quality of tomentum with that of the new variety here described. In the sunlight of a later afternoon, especially in a breeze, the tomentum on leaves and twigs is exposed in an undulating movement, imparting a striking effect. A remarkable combination of three colors is made, when the tree is in bloom, by the leaves glossy green on the upper surface, with the brownish orange tomentum on the under surface, and the white flowers.

New branchlets are covered with a dense coating of velvety brownish orange tomentum comparable to that on the underside of the leaves, as herein described.

It should be emphasized that the leaves of some specimens of *Magnolia grandiflora* have little tomentum. An example of this is the Majestic Beauty (United States Plant Patent No. 2,250), which bears no noticeable tomentum.

Flower buds:

*Size.*—3" to 3½" long, and 1¼" to 1⅝" in diameter.

*Form.*—Narrowly ovoid, with a long and pointed body.

*Growth.*—The bud is enclosed in a stipular spathe which splits longitudinally along a seam, and sometimes laterally along an irregular course. The spathe is coated with a dense, brownish orange tomentum, and is usually cast by the time the flower is ready to open.

The petaloids and petals are imbricated in the bud. The bud opens slowly over several days, depending on the weather.

*Peduncle.*—Erect. About 3/8" in diameter, and 1" to 1¼" in length. Coated with dense, brownish orange tomentum.

Flower:

*Flowering period.*—Blooms from early June to mid-August, with ocassional blooms in May (latter portion), September, and October.

Since plants of this new variety are propagated by grafting, they bloom in the first or second year. This is an advantage to the nurseryman, who will be able to assure a customer that a plant of this variety will bloom the first or second year after planting. Most seedling-grown plants of the species do not bloom for six or ten years.

*Color.*—Creamy white.

*Size.*—6" to 8" in diameter when fully opened.

*Form.*—Single and terminally borne. Bowl or saucer shape when fully opened. Flower has a center spindle or receptacle 1¼" to 1¾" high on which stamens and pistils are imbricated.

*Petalage.*—8 petals, borne in two alternating ranks or tiers above a set of 4 petaloid sepals. The petals and sepals are spatulate and concave in form, and are of a creamy white color throughout. The petals remain on the peduncle for three to five days, or sometimes longer, depending on the weather.

*Petaloids.*—The 4 petaloids and 8 sepals are indistinguishable in color, form, and texture.

*Texture.*—Soft and leathery. Velvety in appearance.

*Discoloration.*—In a bouquet in the house, the petals dry and turn to an apricot color. In this condition they sometimes do not fall for a substantial number of days, and have a most attractive appearance.

*Fragrance.*—All flowers of other *Magnolia grandiflora* noted to date have a strong, rich, sweet fragrance. The flowers of the present variety have a distinct lemon-like fragrance.

*Lasting quality.*—Because of the native range of *Magnolia grandiflora,* the flower performs best in conditions of heat and high humidity. Normally the flower of this new variety lasts for three to five days on the tree, and about the same time as a cut flower.

Floral parts:

*Stamens.*—Creamy yellow in color, imbricated in many ranks at the base of the receptacle, and early deciduous, exposing a bright purple area at the base of the receptacle.

*Anthers.*—Strap-shaped, and cream colored, with purple base. Abundant and indefinite in number.

*Filaments.*—Lower part is bright purple.

*Pollen.*—Golden yellow.

*Pistils.*—Indefinite in number, and densely imbricated on the summit of the receptacle. Style is short and recurved.

*Stigmas.*—Creamy yellow.

*Ovaries.*—Single celled and fleshy.

Fruit:

*Shape.*—Fleshy, narrowly ovate cone, 2¼" to 3½" long, and 1½" to 2" wide at base, tapering slightly to a rounded apex, and standing upright on a peduncle 1" to 1¼" long. Fruit body is comprised of coalescent two-seeded carpels.

*Color.*—As the fruit ripens, the exposed green portions turn to tints of scarlet before dehiscence in October and November, thence to a rusty brown at maturity when the glossy red seeds slowly emerge from the carpels.

*Seeds.*—Upon emergence from the carpels, the seeds are suspended by long, slender, white cords before falling. Two seeds are formed in each carpel. They are less than ½" long, and are triangular in shape.

Desirability: Hundreds of thousands of trees of other *Magnolia grandiflora* have been planted in gardens, in parks, on streetsides and roadsides in the temperate parts of the world. Most of these have been seedling grown and hence vary widely in conformation, foliage, flowers, hardiness, etc.

One of the chief advantages of selected stock, vegetatively grown, is that the morphological and physiological characteristics may be predicted with a surprising degree of accuracy.

Thus, with the introduction of the new variety of *Magnolia grandiflora* herein described, the performance and characteristics of its vegetatively reproduced offspring can be predicted, and which include:

(1) An evergreen, dense appearing tree having a strong structural framework with numerous well-crotched branches and slender, pliable branchlets, simplifying the task of training in the early stages of growth.

(2) Leaves which are glossy green on the upperside and having a dense coating of velvety, brownish orange tomentum on the underside, providing a new type of foliage of *Magnolia grandiflora* for decorative purposes.

(3) Numerous lemon-fragrant flowers of a delicate creamy white, giving the tree a singular note of beauty.

(4) A tree which will produce flowers in the first or second year after planting.

The tree and its flowers herein described may vary in slight detail due to climatic and soil conditions under which the variety may be grown; the present description being of the variety as grown in Saratoga, California.

The following is claimed:

A new and distinct variety of *Magnolia grandiflora* tree, substantially as illustrated and described, characterized—as to novelty and principally in comparison with the Samuel Sommer and the Majestic Beauty—by leaves which are glossy green on the upperside and with a dense coating of velvety brownish orange tomentum on the underside, and numerous lemon-fragrant creamy white flowers normally having twelve petals.

No references cited.

ABRAHAM G. STONE, *Primary Examiner.*

R. E. BAGWILL, *Assistant Examiner.*